(12) United States Patent
Van Driel et al.

(10) Patent No.: US 8,976,350 B2
(45) Date of Patent: Mar. 10, 2015

(54) METHOD FOR DETERMINING CARBON IN CAST IRON

(75) Inventors: Roland Van Driel, Kranenburg (DE); Bruno Van Stuijvenberg, Emmerich (DE)

(73) Assignee: Spectro Analytical Instruments GmbH, Kleve (DE)

( * ) Notice: Subject to any disclaimer, the term of this patent is extended or adjusted under 35 U.S.C. 154(b) by 141 days.

(21) Appl. No.: 13/576,458

(22) PCT Filed: Feb. 17, 2011

(86) PCT No.: PCT/EP2011/000768
§ 371 (c)(1),
(2), (4) Date: Aug. 1, 2012

(87) PCT Pub. No.: WO2011/101143
PCT Pub. Date: Aug. 25, 2011

(65) Prior Publication Data
US 2012/0300204 A1    Nov. 29, 2012

(30) Foreign Application Priority Data
Feb. 22, 2010   (DE) .......................... 10 2010 008 839

(51) Int. Cl.
*G01J 3/30*   (2006.01)
*G01N 21/67*   (2006.01)

(52) U.S. Cl.
CPC ....................................... *G01N 21/67* (2013.01)
USPC ........................................................ 356/313

(58) Field of Classification Search
USPC ................................................. 356/300–334
See application file for complete search history.

(56) References Cited

U.S. PATENT DOCUMENTS

| 4,641,968 A | 2/1987 | Grandy |
| 5,141,314 A | 8/1992 | Belmore et al. |
| 2009/0166584 A1* | 7/2009 | Shimooka et al. ...... 252/301.4 F |

FOREIGN PATENT DOCUMENTS

JP   57141540 A   9/1982

OTHER PUBLICATIONS

International Preliminary Report on Patentability issued in International Application No. PCT/EP2011/000768 dated Aug. 28, 2012.
International Search Report and Written Opinion issued in PCT/EP2011/000768, mailed Jul. 7, 2011 with English translation of International Search Report.
Zhou Z et al., "Arc/Spark Optical Emission Spectrometry: Principles, Instrumentation, and Recent Applications", Applied Spectroscopy Reviews, pp. 165-185, Jan. 1, 2005.

* cited by examiner

*Primary Examiner* — Abdullahi Nur
(74) *Attorney, Agent, or Firm* — Panitch Schwarze Belisario & Nadel LLP

(57) ABSTRACT

A method of determining the carbon content of an iron alloy may include starting of the measurement of a sample in a spark spectrometer, creation of a plasma in a pre-sparking phase, detection and recording of an intensity signal for the carbon, calculation and cutting out of an unstable plasma phase, calculation of an excessive rise in the carbon signal, and calculation of the content of dissolved and undissolved carbon.

9 Claims, 6 Drawing Sheets

| Name of sample | C(%)_new method in percentages by weight | C(%)_old method | C(%) from combustion | Difference between combustion and old method | Difference between combustion and new method |
|---|---|---|---|---|---|
| 1 | 3.63 | 3.54 | 3.62 | 0.083 | 0.007 |
| 1--1 | 3.64 | 3.19 | 3.68 | 0.489 | 0.039 |
| delta | 0.010 | 0.350 | 0.056 | | |
| 2 | 3.68 | 3.5 | 3.64 | 0.143 | 0.037 |
| 1--2 | 3.64 | 3.24 | 3.64 | 0.396 | 0.004 |
| delta | 0.040 | 0.260 | 0.007 | | |
| 3 | 3.68 | 3.4 | 3.64 | 0.237 | 0.043 |
| 1--3 | 3.75 | 3.13 | 3.61 | 0.482 | 0.138 |
| delta | 0.070 | 0.270 | 0.025 | | |
| 4 | 3.73 | 3.43 | 3.69 | 0.261 | 0.039 |
| 1--4 | 3.62 | 3.2 | 3.68 | 0.482 | 0.062 |
| delta | 0.110 | 0.230 | 0.009 | | |
| 5 | 3.66 | 3.42 | 3.63 | 0.208 | 0.032 |
| 1--5 | 3.66 | 3.19 | 3.65 | 0.458 | 0.012 |
| delta | 0.000 | 0.230 | 0.020 | | |
| 6 | 3.7 | 3.41 | 3.65 | 0.236 | 0.054 |
| 1--6 | 3.74 | 3.17 | 3.67 | 0.503 | 0.067 |
| delta | 0.040 | 0.240 | 0.027 | | |
| 7 | 3.74 | 3.43 | 3.65 | 0.224 | 0.086 |
| 1--7 | 3.7 | 3.18 | 3.69 | 0.505 | 0.015 |
| delta | 0.040 | 0.250 | 0.031 | | |
| 8 | 3.66 | 3.58 | 3.59 | 0.009 | 0.071 |
| 1--8 | 3.62 | 3.29 | 3.66 | 0.374 | 0.044 |
| delta | 0.040 | 0.290 | 0.075 | | |
| 9 | 3.63 | 3.42 | 3.62 | 0.195 | 0.015 |
| 1--9 | 3.62 | 3.12 | 3.62 | 0.496 | 0.004 |
| delta | 0.010 | 0.300 | 0.001 | | |

FIG. 8

METHOD FOR DETERMINING CARBON IN CAST IRON

CROSS REFERENCE TO RELATED APPLICATIONS

This application is a National Phase filing under 35 U.S.C. §371 of PCT/EP2011/000768 filed on Feb. 17, 2011; and this application claims priority to Application No. 102010008839.0-52 filed in Germany on Feb. 22, 2010; the entire contents of these are hereby incorporated by reference.

The present invention relates to a method of determining carbon in cast iron, in particular in spheroidal graphite cast iron, using spark spectrometry applied to a solid sample.

Spark spectrometry is a method of analysing the chemistry of metals. An electrical discharge is produced which vaporises part of the sample and generates a plasma. In this plasma, the atoms of the sample are excited and produce emission lines which are characteristic of the elements contained in the sample. Analyses of this kind are routinely made in the steel industry to check alloys.

This method of measurement gives measurements of very high accuracy. However, it has long been known that in alloys spark spectrometry is only to measure the carbon fraction exactly when the carbon is present in the alloy in fully dissolved form. Carbon which precipitates in elemental form, of the type which is present in spheroidal graphite cast iron for example, regularly results in the measurements being falsified. The measurements made of the carbon fraction in such alloys are too low.

In spark spectrometry, a metal sample first has sparks applied to it under an atmosphere of shielding gas. In this so-called pre-sparking phase, the surface of the sample is rendered homogeneous by high-energy sparks at a frequency from 200 to 800 Hz. In the process, each spark melts the surface of the sample around its point of impact to a radius of a few tens of micrometers. After the pre-sparking phase, this homogenised surface can be exposed to the measuring sparks proper which generate the signal to be analysed. If precipitated elemental carbon or other precipitated elements or compounds such as $Al_2O_3$ are present, the pre-sparks prefer to attack the grain boundaries of these precipitates. In the case of carbon, this results in the elemental carbon being sublimed and removed from the sample. Hence the parts of the surface of the sample which have been homogenised by pre-sparking contain less carbon than the original alloy.

In practice, this problem is avoided by cooling the liquid sample which is taken as quickly as possible. In this way, the carbon present is not precipitated in elemental form. This process does not have good repeatability in practice. It results in there being samples which cool at different rates and hence which have different contents of elemental carbon. Therefore, when the correctness of the analysis has to meet more stringent requirements, there is no alternative but to use different methods of analysis to determine carbon. A common alternative method of analysis is to machine a sample and subject it to controlled combustion. The carbon dioxide which is produced when this is done is measured and the total carbon content of the sample is determined from it. This method is very costly because it takes time and calls for additional expenditure on apparatus.

It is therefore an object of the present invention to specify a method by which the carbon content of alloys can be precisely measured by spark spectrometry even when the carbon is present in elemental form.

This object is achieved by a method which has the features of claim 1.

Because the intensity signal for carbon is recorded back in the pre-sparking phase, allowance can be made for the carbon fraction which is removed by sublimation on the alloy. If the carbon concentration is measured in the conventional way after the pre-sparking phase and allowance is made for the previously determined quantity of sublimed carbon, the measured value is corrected in this way by the carbon fraction which was sublimed and the correct result is determined for the carbon fraction in the sample.

It is advantageous in this case for the carbon signal at a wavelength of 148.176 nm to be measured in this case. The pre-sparking phase is preferably carried out over a period of from 8 to 15 sec. and in particular of 12 sec. Particularly good monitoring of this method becomes possible if the signal for iron too is detected during the pre-sparking phase. The point in time from which there is also a stable signal meaningful for the subliming carbon in the pre-sparking phase can be determined from the signal for iron. The iron line at 149 nm is preferably measured in this case.

The present invention will be described in detail below by reference to the drawings. In the drawings:

FIG. 8 shows a table of comparison results as obtained with conventional spark spectrometry, the new method, and combustion analysis with CO2 determination.

Figure 1:
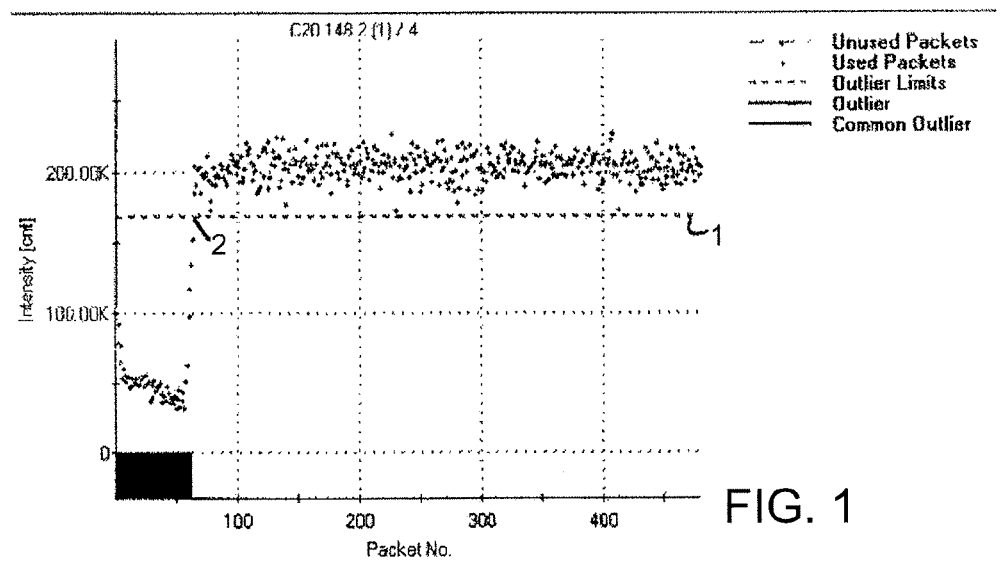
FIG. 1 shows the intensity distribution in the pre-sparking phase for samples whose carbon fraction is fully dissolved.

Shown in FIG. 1 is the curve for intensity over time which was measured in the pre-sparking phase at the carbon line at 148.176 nm. What in particular is shown are the numbers of the measurement intervals along the X-axis, starting at 0. Each measurement interval was approximately 0.025 sec. The scanning frequency was therefore 40 Hz. The graph maps a pre-sparking phase lasting approximately 12 sec.

Shown along the Y-axis in random units is the intensity of the radiation, which is approximately proportional to the number of photons measured. In the example shown in FIG. 1, the intensity varied from approximately 50,000 per measurement interval to around 200,000 per measurement interval. The first measurement intervals gave a signal of only about 50,000 units. It is during this so-called sparking-in phase that the plasma forms. The length of this phase varies widely and depends on, for example, contamination on the surface of the sample. After that the signal rises to about 200,000 units. All that is shown in FIG. 1 relates only to the usual pre-sparking phase in which the sample is first rendered homogeneous in a spark spectrometer. There is no evaluation of this pre-sparking phase in the known methods of measurement.

In the present method, the data from the pre-sparking phase shown in FIG. 1 is processed. For this purpose, signals lying below a threshold value 1 are discarded. What this actually means in the case of FIG. 1 is that approximately the first 60 measurement intervals are discarded until the limiting value 1 is exceeded at about point 2 in the course of a rise. The mean value of intensity from point 2 on is looked at in order to calculate the carbon content from the pre-sparking phase.

Figure 2:
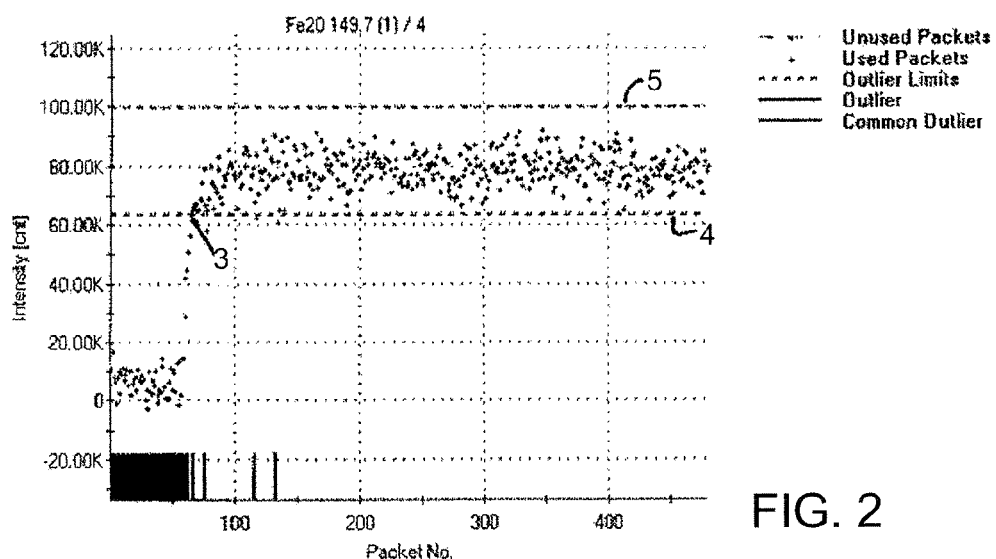
FIG. 2 shows the intensity distribution in the pre-sparking phase for the iron fraction in the sample shown in FIG. 1.

FIG. 2 shows the corresponding iron signal at the 149.653 nm line. In FIG. 2 as well it can be seen that the intensity is about 5,000 units per measurement interval in the first 60 measurement intervals. After that there is a very steep rise in intensity and it exceeds a lower limiting value 4 at a point 3. From point 3 on, the mean value of the pulses per measurement interval is approximately 75,000 units. For the signal for iron too the plasma is unstable until point 3 in the pre-sparking phase. These measured values were discarded. From point 3 on the signal from the pre-sparking phase was evaluated. In this case an upper limiting value 5 was defined in addition with, in the evaluation, individual measurement intervals which were below the lower limiting value 4 or above the upper limiting value 5 being discarded. The signal for iron can be calculated from the intensities between the limiting values.

It should be mentioned that FIGS. 1 and 2 show only the pre-sparking phase, which is also provided in conventional methods and which is intended to be used to render the sample homogeneous. It is from this phase that the actual measuring phase follows on both in the prior art and in a preferred embodiment of the invention. However, in FIGS. 2 and 3 the signals shown are already sufficiently stable from points 2 and 3 on for measured values to be able to be obtained from them for the purpose of calculating the concentration of the element carbon.

The sample shown in FIGS. 1 and 2 is one which does not contain any precipitated elemental carbon. In them the measured values are stable over time. It can be expected that, with such an ideal sample, the signal for carbon will be correctly measured during the measuring phase proper.

Figure 3:
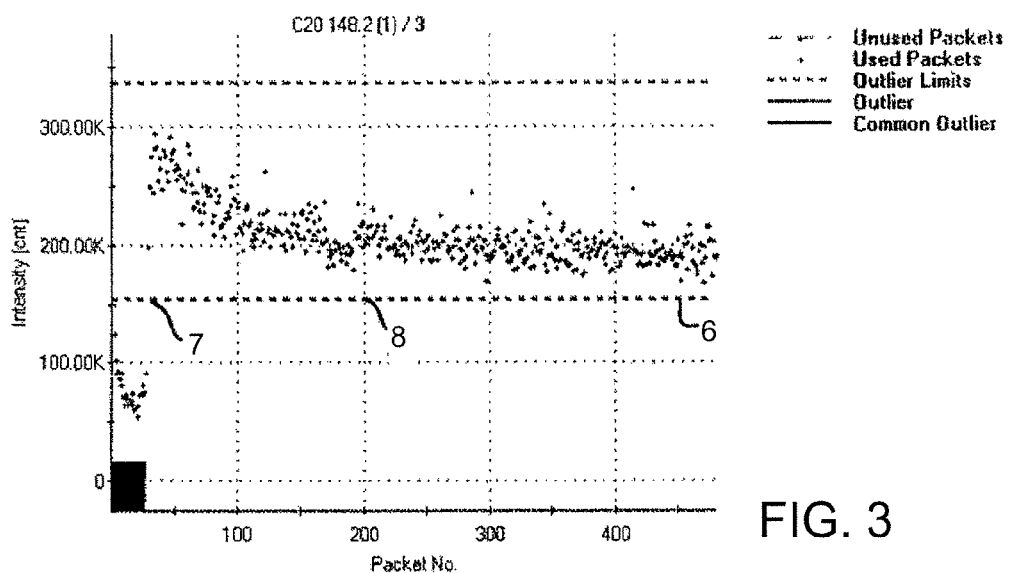
FIG. 3 shows the intensity distribution for a sample containing elemental carbon during the pre-sparking phase.
Figure 4:
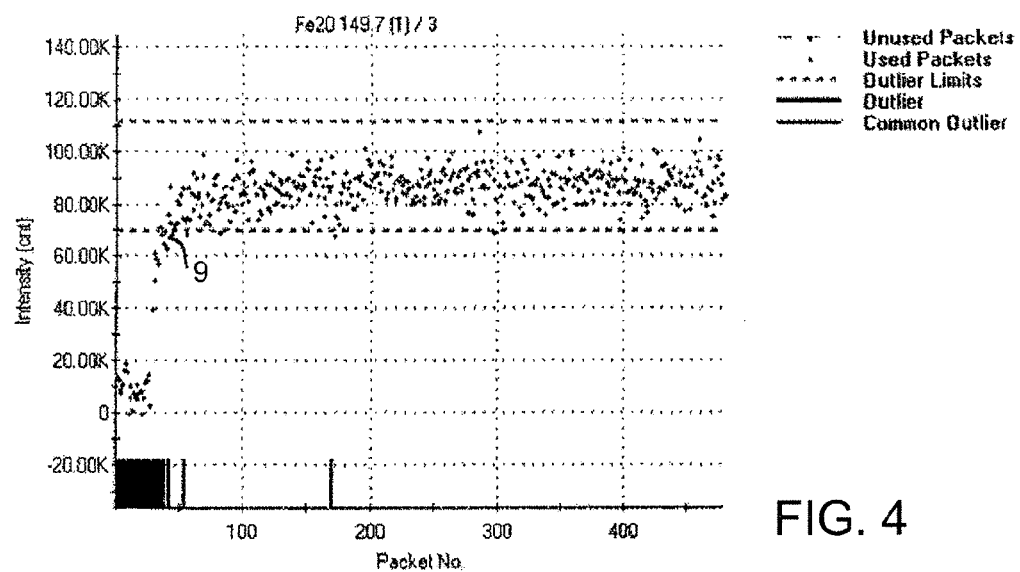
FIG. 4 shows the signal for iron for the sample shown in FIG. 3.

The measurements made on a non-ideal sample containing carbon which had precipitated out are shown in FIGS. 3 and 4. Specifically, FIG. 3 once again shows the curve followed by the intensity of the carbon line at 148.2 nm as in FIG. 1. The other measured parameters are the same. The length of the measurement period shown was likewise about 12 sec. The intensities were initially around 50,000 units and rose rapidly after that point. A lower limiting value of approximately 150,000 units is identified as 6. The lower limiting value 6 is exceeded approximately in measurement interval no. 25 at point 7. The measured points situated before point 7 in time represent the unstable plasma. As from point 7, the measured points were evaluated.

In FIG. 3 it can be seen that the intensities first rise to approximately 300,000 units per measurement interval and then decline approximately exponentially to an almost constant intensity of 200,000 units per measurement interval. Up to approximately measurement interval 200, which is identified as 8, there is an excessive rise in intensity, in contrast to the subsequent continuous signal. This excessive rise is attributable to the subliming carbon which emerges from the sample and which is first measured in the sublimation phase, though after that is lost to measurement. The excessive rise between points 7 and 8 in FIG. 3 thus represents the carbon fraction which was lost due to the sample being made homogeneous.

Finally, FIG. 4 shows the signal for iron at the 149.7 nm line, which signal was recorded for the sample to which FIG. 3 relates. Here too the sparking-in phase is situated before point 9. From point 9 on, i.e. from approximately measurement interval 45 on, the signal can be recorded and evaluated.

Figure 5:
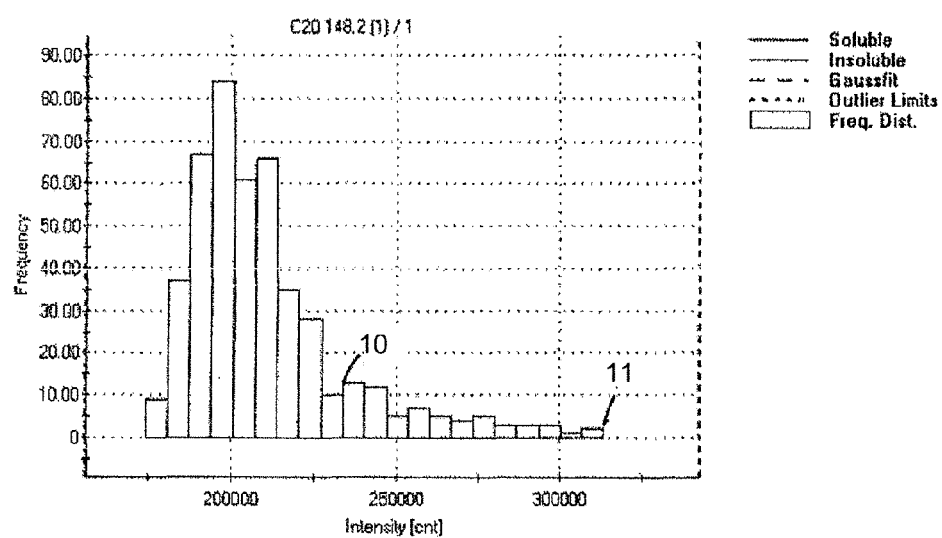
FIG. 5 shows an intensity distribution of the signal shown in FIG. 3 as a bar chart.

FIG. 5 is a schematic view showing the frequency distribution of the individual intensities as a bar chart. Plotted along the x-axis are the intensities, which in FIG. 3 were detected for each individual point of measurement. Shown along the y-axis is the number of measurement intervals in which the corresponding intensity was measured. The shape of this representation is approximately that of a Gaussian function with its maximum at 200,000 units per measurement interval, as was expected from FIG. 3. However, from an intensity of approximately 230,000 on, which is identified by point 10, an outlier running to higher intensities can be seen. This outlier extends from approximately 240,000 to more than 300,000 units per measurement interval. The upper limit is identified by the number 11.

The high values of intensity between points 10 and 11 correspond to the excessive rise in the measured values in FIG. 3 between points 7 and 8. These measured values are to be looked at for the purpose of determining elemental carbon.

Figure 6:
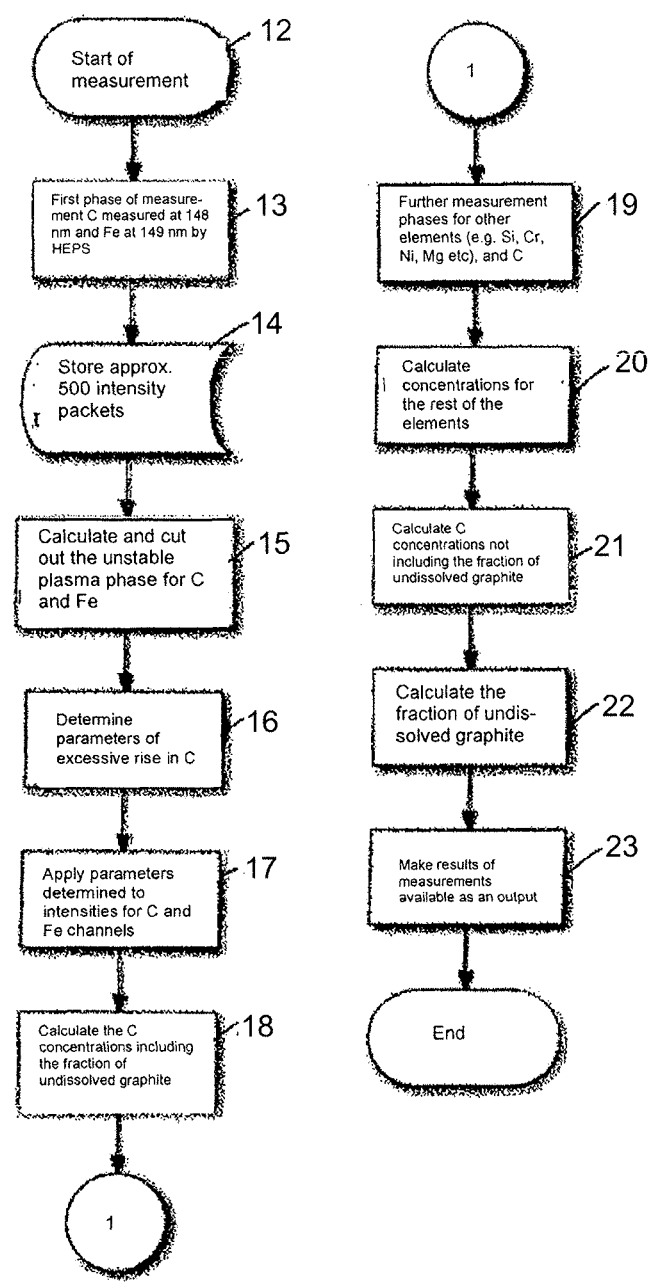
FIG. 6 is a flow chart for the various steps of the method of measurement according to the invention.

The method of measurement itself is shown in a preferred embodiment in FIG. 6. The flow chart in FIG. 6 first makes provision for the start of measurement at 12. At 13, carbon is measured at 148.2 nm and iron at 149.7 nm in the first phase of measurement. A total of some 500 measurement intervals are recorded. This is represented by step 14 of the method. In step 15 of the method, calculations are made for carbon and iron for the unstable plasma phase, which is situated before point 2 in FIG. 1, before point 3 in FIG. 2, before point 7 in FIG. 3 and before point 9 in FIG. 4. The measured values lying before these points are discarded. In step 16 of the method, parameters of the excessive rise in the signal for carbon are determined, i.e. the period between points 7 and 8 in FIG. 3 or the intensity distribution between points 10 and 11 in FIG. 5 is evaluated.

In a step 17 of the method, it is decided which measurement intervals are to be looked at in order to obtain summed intensities for carbon and iron. In step 18 of the method, the carbon concentration in the sample is then calculated from the summed intensities, which concentration includes the fraction of undissolved graphite, which can be calculated due to the excessive rise in the measurement values. Step 18 of the method brings the pre-sparking phase of the measurement process to an end. This is following by the measurement proper, which is carried out as in the prior art. In a step of the method for which the overall reference is 19, the other elements, such for example as silicon, chromium, nickel, magnesium, and also carbon are measured. In step 20 the concentration in the sample is measured for the elements other than carbon. In step 21 of the method, the carbon concentration is then calculated in the conventional way from the stable measurement signal, the carbon fraction in the form of undissolved graphite not being included in the calculation. Then, in step 22, the carbon fraction in the form of undissolved graphite is calculated by finding the difference between the total carbon content available after step 18 and the content of dissolved carbon which was determined in step 21. The result of the measurement finally becomes available as an output in step 23. Given in the output may be both the total carbon content and separate measurements for the fraction of dissolved carbon and the fraction of undissolved carbon respectively.

Evaluation of the excessive rise in the carbon signal in the pre-sparking phase between points 7 and 8 or 10 and 11 thus makes it possible for the undissolved carbon to be taken into account in the measurement.

Figure 7:
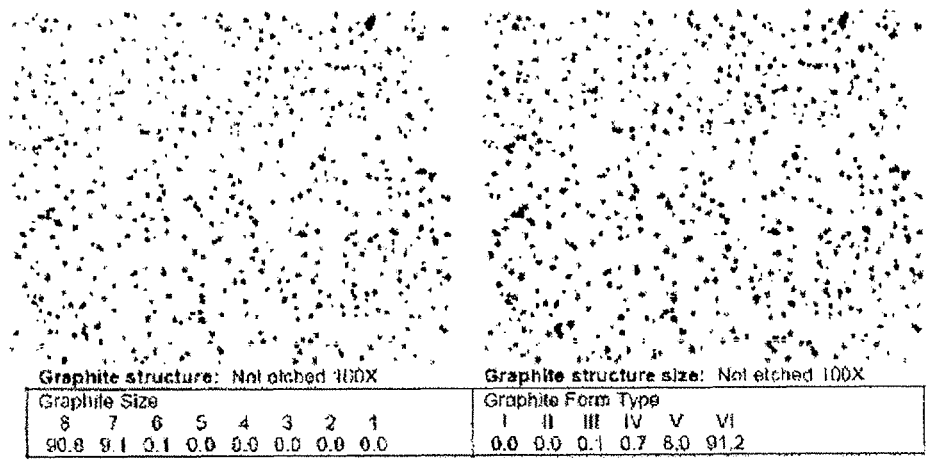
FIG. 7 shows micro-sections of samples containing elemental carbon which has precipitated in spheroidal form.
Figure 7:
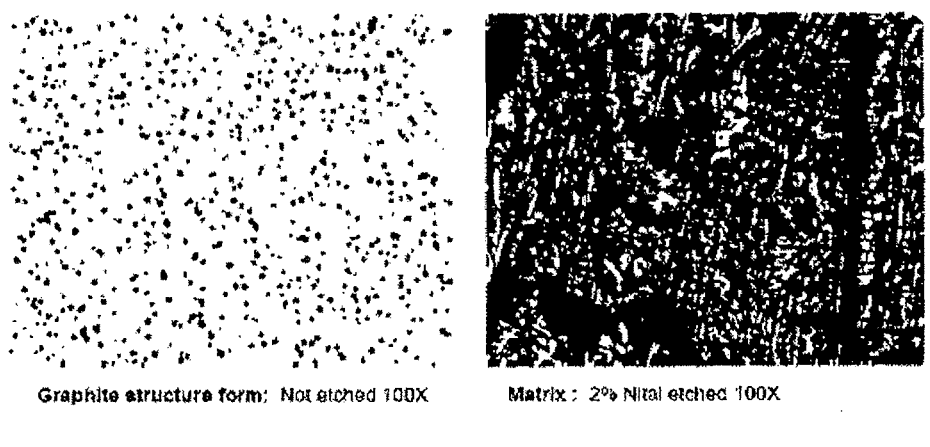

FIG. 7 has been included as an example to show the structure of the sample used for FIGS. 3 and 4. Shown in FIG. 7 at ×100 magnification are microscopic images which show the fraction of spheroidal graphite in spheroidal graphite cast iron. This fraction of spheroidal graphite can be detected by the method according to the invention.

FIG. 8 shows a comparison of the results for a sample such as is shown in FIG. 7, as obtained with conventional spark spectrometry, the new method and combustion analysis with CO2 determination. The figures given as percentages are percentages by weight of carbon. It can be seen that, at carbon contents of approximately 3.6% to 3.7% and as dictated by the nature of the sample, the difference between the conventional method of spark spectrometry and combustion analysis was between 0.08% and 0.5% absolute whereas for the same samples and the new method a difference of between 0.004% and 0.14% absolute was obtained. The difference between the conventional method and combustion analysis was systematically towards the carbon contents being lower whereas the differences between the new method and combustion analysis produced measured values which were in some cases statistically higher and in some cases statistically lower. No systematic difference was apparent.

This shows that with the conventional method it has systematically not been possible to detect the elemental or undissolved carbon, whereas the new method takes into account even this fraction of the carbon.

LIST OF REFERENCE NUMERALS

1. Threshold value
2. Point
3. Point
4. Lower limiting value
5. Upper limiting value
6. Lower limiting value
7. Point
8. Measurement interval
9. Point
10. Point
11. Upper limit
12. Start
13. First phase of measurement
14. Step of the method
15. Step of the method
16. Step of the method
15. Step of the method
17. Step of the method
18. Step of the method
19. Step of the method
20. Step of the method
21. Step of the method
22. Step of the method
23. Step of the method

The invention claimed is:

1. A method of determining carbon content of an iron alloy, the method including:
   (a) starting measurement of a sample of the iron alloy in a spark spectrometer,
   (b) creating a plasma in a pre-sparking phase,
   (c) detecting and recording an intensity signal for carbon,
   (d) calculating and cutting out an unstable plasma phase,
   (e) calculating an excessive rise in the carbon intensity signal, and
   (f) calculating content of dissolved and undissolved carbon of the sample of the iron alloy.

2. The method according to claim 1, wherein the method further comprises:
   (g) measuring carbon concentration in a conventional way following any one of (c), (d), (e), or (f).

3. The method according to claim 1, wherein the method further comprises measuring elements other than carbon in a conventional way following any one of (c), (d), (e), or (f).

4. The method according to claim 1, wherein the method further comprises outputting a result of (f) in the form of a concentration of a fraction of dissolved carbon.

5. The method according to claim 1, wherein in a first phase of measurement, a carbon signal at a wavelength of 148.176 nm is measured.

6. The method according to claim 1, wherein the pre-sparking phase is carried out for a period of 8 sec. to 15 sec.

7. The method according to claim 1, wherein a signal for iron is also detected and recorded during the pre-sparking phase.

8. The method according to claim 1, wherein the method further comprises measuring an iron emission line at 149.653 nm.

9. The method according to claim 1, wherein the content of dissolved and undissolved carbon are output as separate quantities.

* * * * *